United States Patent [19]
Scheller et al.

[11] Patent Number: 4,722,224
[45] Date of Patent: Feb. 2, 1988

[54] ULTRASONIC SENSOR FOR THE DETECTION OF GAS BUBBLES

[75] Inventors: Thomas Scheller, Munich; Werner Heinze, Windach; Johann Schreyer, Munich; Roman Wysotzky, Bad Tolz, all of Fed. Rep. of Germany

[73] Assignee: Shiley Inc., Irvine, Calif.

[21] Appl. No.: 901,214

[22] Filed: Aug. 27, 1986

[30] Foreign Application Priority Data

Aug. 28, 1985 [DE] Fed. Rep. of Germany ....... 3530747

[51] Int. Cl.⁴ ............................................. G01N 29/00
[52] U.S. Cl. ........................................... 73/599; 73/600
[58] Field of Search ........................ 73/644, 599, 61 R

[56] References Cited
U.S. PATENT DOCUMENTS

| 3,663,842 | 5/1972 | Miller | 73/644 |
| 3,798,961 | 3/1974 | Flambard et al. | 73/644 |
| 3,974,681 | 8/1976 | Namery | 73/600 |
| 4,214,484 | 7/1980 | Abts | 73/644 |
| 4,235,095 | 11/1980 | Liebermann | 73/61 R |
| 4,483,343 | 11/1984 | Beyer et al. | 73/644 |
| 4,542,644 | 9/1985 | Claytor et al. | 73/599 |
| 4,579,123 | 4/1986 | Chen et al. | 73/644 |

FOREIGN PATENT DOCUMENTS

| 0053453 | 6/1982 | European Pat. Off. . |
| 2732550 | 3/1978 | Fed. Rep. of Germany . |
| 3503477 | 8/1985 | Fed. Rep. of Germany . |
| 1418181 | 12/1975 | United Kingdom . |

Primary Examiner—Stewart J. Levy
Assistant Examiner—Louis M. Arana
Attorney, Agent, or Firm—Peter C. Richardson; Larry C. Akers; Roger C. Turner

[57] ABSTRACT

An ultrasonic sensor for non-invasive detection of air bubbles in a liquid flowing through a tube comprises two half-housings capable of being assembled together and two mutually opposed ultrasonic transducers, one installed in each of the half-housings. For acoustic coupling of the tube to the two mutually opposed ultrasonic transducers, each half-housing contains a chamber closed off by a flexible membrane and filled with a fluid highly transmissive of sound. The fluid displaced by the tube inserted between the two half-housings forces the membrane up in the form of a bulge on either side of the tube. In this way, an excellent contact is obtained between the chamber filled with sound-transmissive fluid and the tube. The membrane may be embedded into the side walls of the half-housings and cylindrically arched along the same.

15 Claims, 5 Drawing Figures

ULTRASONIC SENSOR FOR THE DETECTION OF GAS BUBBLES

BACKGROUND OF THE INVENTION

The invention relates to an ultrasonic sensor for non-invasive detection of gas bubbles in a liquid flowing through a tube, comprising two half-housings capable of being assembled together in which the tube is laid; two ultrasonic transducers facing each other, one acting as transmitter and the other as receiver and one installed in each of the half-housings; and transmission links disposed one in front of each transducer for acoustic coupling to the interposed tube carrying the liquid.

Such ultrasonic sensors are employed wherever a liquid flowing in a pipe or tube must be tested for the presence of gas bubbles, with no intervention in the liquid circuit being allowed during the testing. For example, an extrocorporeal circulation of blood must be continuously monitored with utmost dependability so that no air bubbles, dangerous to the patient, can enter the bloodstream. To detect gas bubbles, the flexible or other tube carrying the liquid is placed between the two ultrasonic transducers. If the tube is completely filled with liquid, the sound waves emanating from the one ultrasonic transducer will be transmitted unimpeded to the opposed transducer acting as receiver. But if gas bubbles traverse the sonic field, the sound waves will be damped thereby, leading to distinct amplitude variations in the received signal.

Ultrasonic sensors operating on this principle are known in a variety of forms. European Published Patent Application No. 53,453, for example, discloses an ultrasonic sensor in which the two mutually opposed ultrasonic transducers are installed in a common one-piece housing. In front of the transducers, elastic transmission links are disposed, between which the tube carrying the liquid can be grasped. There are known devices having two half-housings capable of being applied to the tube from either side, in which case transmission links of elastic material are likewise provided for acoustic coupling (e.g. U.S. Pat. No. 3,663,842). These known ultrasonic sensors have the disadvantage that their use is limited to a single determinate tube diameter, or that their more or less elastic grasping means compress the tube carrying the liquid at the point of measurement. Any local variation in cross section leads immediately to a rise in flow velocity and to a risk of inducing turbulence in the stream of liquid. Consequently, errors of measurement as well as undesired changes in the liquid being monitored can occur. For example, when the liquid is blood there is a danger that blood corpuscles may be destoryed. owing to imperfect contact between the tube and transmission links, furthermore, the acoustic coupling between the ultrasonic transducers and the tube carrying the liquid is unsatisfactory. This problem is only partially remedied by the use of so-called ultrasonic coupling jelly.

SUMMARY OF THE INVENTION

It is an object of the present invention to provide an ultrasonic sensor of the aforementioned kind which, while avoiding the disadvantages outlined above, may readily be applied to tubing of different diameters without any significant deleterious deformation of the tubing and, in particular, ensures a good acoustic coupling.

This and other objects are achieved with an ultrasonic sensor for non-invasive detection of gas bubbles in a liquid flowing through a tube, comprising two half-housings capable of being assembled together in which the tube is laid; two ultrasonic transducers facing each other, one acting as transmitter and the other as receiver and one installed in each of the half-housing; and transmission links disposed one in front of each transducer for acoustic coupling to the interposed tube carrying the liquid, with the transmission links each comprising a chamber closed off by a flexible membrane and filled with a fluid highly transmissive of sound. When the ultrasonic sensor according to the invention is applied to a tube, the displaced fluid in said chambers forces the membrane up in the manner of a bulge on either side of the tube. In this way, a large area of secure contact with the tube is provided. By means of the liquid enclosed in the chamber, this liquid being a good conductor of sound, an optimum acoustic coupling of the ultrasonic transducer in question is obtained and the use of ultrasonic coupling jelly may be dispensed with. Since the flexible membrane wraps itself around the tube like a soft cushion, the tube suffers no significant deleterious deformation, so that undesired turbulence in the stream of liquid is avoided.

In preferred embodiment of the invention, the walls of the half-housings are substantially U-shaped in cross section, the fluid-filled chambers are bounded by the side walls of the half-housings, the respective members are stretched between said side walls, and the ultrasonic transducers are disposed at the bases of the half-housings. In the ultrasonic sensor so constructed, the chambers filled with the sound-conductive liquid, representing the transmission links, are integrated in the half-housings. The U-shaped cross section of the half-housings necessarily provides a trough-like cavity, remaining only to be closed off by the membrane stretched between the side walls. This preferred ultrasonic sensor is therefore simple and inexpensive to produce. Additionally, a tube introduced between the two half-housings and resting on the flexible membranes is also supported at the sides by the elevated lateral surfaces representing the flanges of the "U", and hence is supported in all directions.

In another preferred embodiment, the membrane is drum-shaped along the side walls of the half-housing, in particular circularly arched. This leads to a uniform distribution of contact pressure over the adjacent tube and permits use for different tube diameters. The arching of the membrane may be flattened in the neighborhood of the vertex, for example by reducing the fluid pressure within the chamber, to enlarge the area of contact with the inserted tube.

A good seal of the fluid-filled chambers is achieved if the side edges of the membranes are embedded into the side walls of the half-housings.

In an especially advantageous embodiment of the ultrasonic sensor of the invention, the side walls of the half-housing comprise a portion formed in one piece therewith and having a recess and an attached side portion shaped to match this recess, and the membrane is secured between the portion so formed and the side portion. The two-piece construction of the side walls permits an especially simple and fluid-tight installation of the flexible membrane. The desired arching in an arc of a circle is imparted to the membrane if the attached side portions are in the shape of a segment of a circle and the side edges of the membrane are inserted between these side portions and the fixed portions, having a matching circular recess, of the side walls.

To accommodate the fluid contained in the membrane that is displaced upon insertion of a tube, grooves may be provided in the half-housings around the membrane. The clearances provided in this way permit the fluid cushion to yield laterally and hence provide an especially good adaptation to different tube diameters. Preferably, the grooves in the side walls are rectangular in cross section, while the grooves in the base of the half-housing are adapted to the curvature of the membrane and are triangular in cross section. To achieve, a high degree of pliability, the membrane is preferably made of a synthetic material having rubber-like elasticity.

In another especially preferred embodiment of the invention, special guide strips are provided on both half-housings above the membrane, pointing inward from the side walls of the half-housing. If these guide strips extend far enough laterally to reach the inserted tube, they will ensure an exact orientation of the tube at all times in relation to the ultrasonic transducer installed in the top or bottom half, as the case may be, of the housing. A lateral deflection of the tube, due for example to flexible deformation thereof, is effectively prevented by this lateral stabilization. The entire liquid-carrying cross section of the tube is therefore always within the ultrasonic field; even if the tube is carelessly inserted or too large in diameter, proper bubble detection is ensured. Since a tube somewhat too large in diameter cannot escape laterally, and therefore can at worst assume the cross sectional shape of a vertically erect oval, the guide strips moreover will prevent an otherwise possible constriction of the tube walls, which in an extremely unfavorable case might even lead to direct contact between the two opposed membranes and hence to an acoustic short circuit. Independently of the precise maintenance of a given diameter of the tube used or its careful placement between the two half-housings, an ultrasonic sensor equipped with the said guide strips will therefore operate dependably and without trouble. A slight inflexion of the guide strips over their lengthwise direction will facilitate contact of the flexible membrane with the outside wall of the tube over a segment of maximum length.

In an appropriate refinement of the invention, the two half-housings are hinged together by an articulation. This facilitates insertion of a tube carrying the liquid to be monitored for gas bubbles into the ultrasonic sensor. A clasp may advantageously be disposed on the sides of the half-housings opposed to bhe articulation, whereby the ultrasonic sensor may be locked up after the tube has been inserted.

DETAILED DESCRIPTION OF THE INVENTION

The invention will be described in detail with reference to various preferred embodiments thereof. Reference to these embodiments does not limit the scope of the invention, which is limited only by the scope of the claims. In the drawings:

Figure 1:
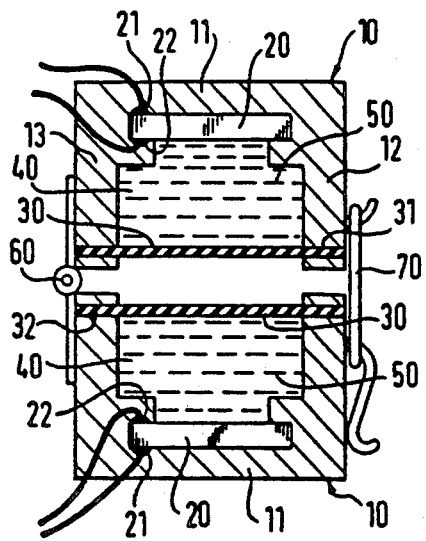
FIG. 1 shows an ultrasonic sensor of the invention having two half-housings of U-shaped cross section joined by an articulation, in vertical section.

The ultrasonic sensor shown in FIG. 1 comprises two substantially like half-housings 10. At the base 11 of each, an ultrasonic transducer 20 is disposed. These consist of piezoceramic material, and each is provided with electrical connection contacts 21, 22 at the top and bottom. Between the side walls 12 and 13 of each half-housing 10, a membrane 30 of synthetic material with rubber-like elasticity is stretched. The half-housings 10 are U-shaped in cross section. Their side walls 12, 13 together with the transducers 20 at the bases 11 form chambers 40, closed off by the flexible membranes 30. The interiors of chambers 40 are completely filed with a fluid 50 highly transmissive of sound. An articulation 60 joins the two half-housings 10. On the opposed side, a clasp 70 is attached.

Figure 2:
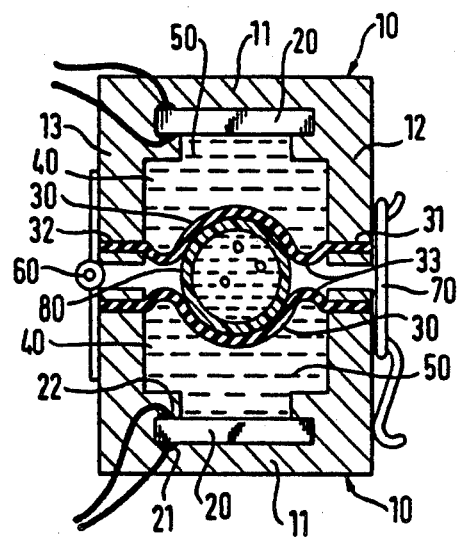
FIG. 2 shows the ultrasonic sensor of FIG. 1 with a tube inserted between the half-housings, likewise in vertical section.

FIG. 2 shows a tube 80 placed in the ultrasonic sensor of FIG. 1, through which tube flows the liquid to be monitored for possible presence of gas bubbles. The fluid 50 displaced by the tube 80 forces the membranes 30 up on either side at 33 in the manner of a bulge. The membranes 30 are thus each in contact with the tube 80 over about half its periphery, with no interspace. The chambers 40 constitute transmission links in front of the two ultrasonic transducers 20. The sound waves emanating from one transducer 20, acting as the transmitter, are transmitted to the tube 80 largely unimpeded by the fluid 50, a good conductor of sound. Any gas bubbles present in the liquid passing through the tube 80 will sharply reduce the intensity of the sound wves received by the opposed ultrasonic transducer 20, acting as the receiver. The large area of contact between the fluid 50 enclosed by the membrane 30 and the tube 80 ensures an excellent acoustic coupling of the ultrasonic transducers 20.

Figure 3:
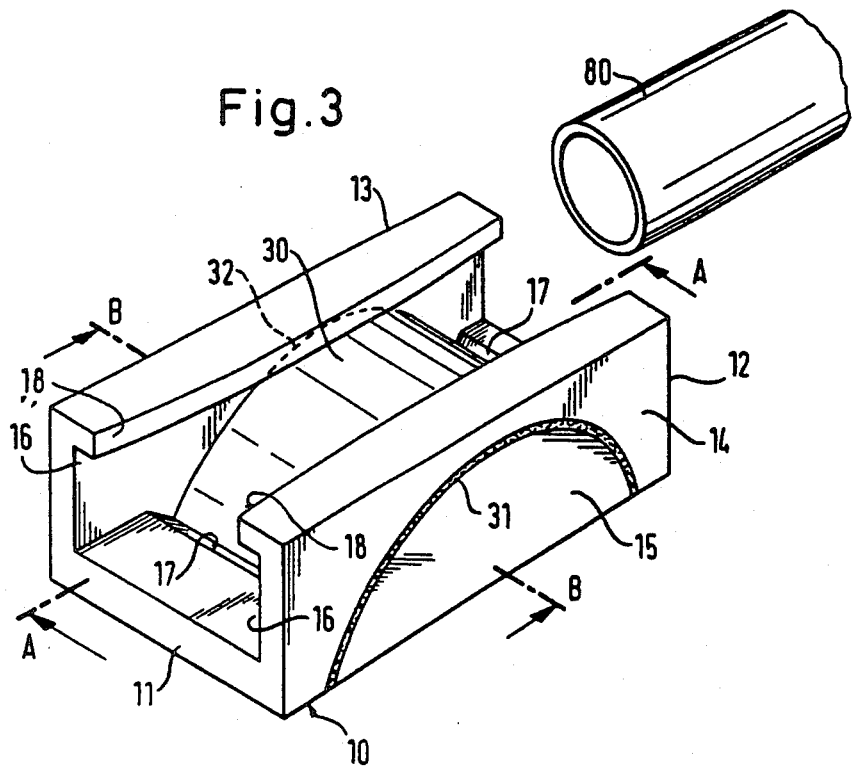
FIG. 3 shows a half-housing of an ultrasonic sensor of the invention, having a U-shaped cross section and provided with additional grooves and guide strips, with a semicircularly-arched membrane, as well as a cut-off length of tubing to be inserted, all in perspective view.

In the half-housing 10 shown in FIG. 3, the membrane 30 is arched in a circular arc along the side walls 12, 13. Each side wall 12, 13 has a fixed formed portion 14 with a circular arc recess, in which a matching side portion 15 with a matching circular shape is inserted.

Figure 4:
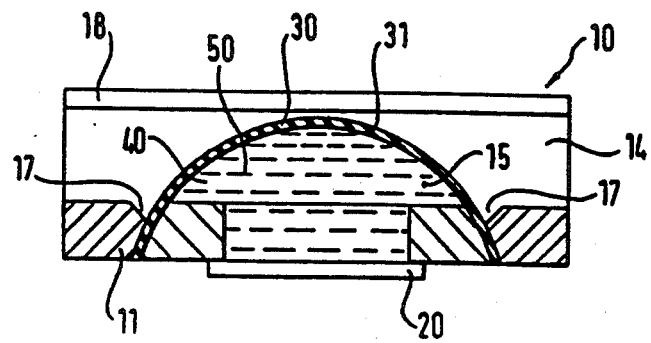
FIG. 4 shows the half-housing of FIG. 3 in vertical section taken along the line A—A.
Figure 5:
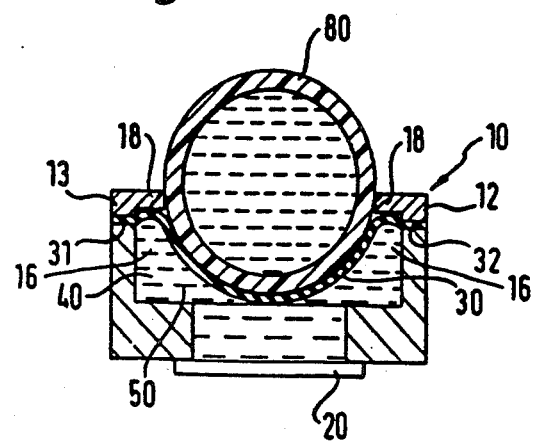
FIG. 5 shows the half-housing of FIG. 3 with tube inserted, in vertical section taken along the line B—B.

As may be seen in FIGS. 3 to 5, the side edges 31, 32 of the membrane 30 are secured between the formed portion 14 and the side portion 15. Grooves 16 of rectangular cross section are provided in the side walls 12, 13 on the inside. In the base 11 of the half-housing, grooves 17 of triangular cross section are provided. the clearances provided by these grooves 16, 17 serve to accommodate the fluid 50 contained by the membrane 30 and displaced on insertion of the tube 80 (compare FIGS. 2 and 5). The side walls 12, 13 serve at the same time for lengthwise guidance of the tube 80. Two special guide strips 18 are provided on each of the half-housings 10, projecting inwardly from the side walls 12, 13 above the membrane 30. The guide strips 18 extend laterally all the way to the inserted tube 80, so that the tube cannot escape to the right or left but at most upward and downward. The guide strips 18 are slightly convexly inflected in their lengthwise direction (see FIG. 3).

We claim:

1. An ultrasonic sensor for non-invasive detection of gas bubbles in a liquid flowing through a tube comprising two housing portions, each substantially U-shaped in cross section, capable of being assembled together and adapted to receive said tube when so assembled: an ultrasonic transducer installed at the base of each of said housing portions facing each other, with one acting as a transmitter and the other as a receiver; and a transmission link disposed in front of each transducer for acoustic coupling to the interposed tube carrying said liquid, with each of said transmission links comprising a chamber closed off by a flexible membrane and filled with a fluid highly transmissive of sound with said fluid-filled chambers bounded by the side walls of the housing portions and arched along said side walls.

2. An ultrasonic sensor of claim 1 wherein the arching of each membrane follows a circular arc.

3. An ultrasonic sensor of claim 1 wherein the arching of each membrane is flattened in the neighborhood of the arch vertex.

4. An ultrasonic sensor of claim 1 wherein the side edges of the respective membranes are embedded in the side walls of the respective housing portions.

5. An ultrasonic sensor of claim 4 wherein the side walls of each housing portion comprise a portion formed in one piece therewith and having a recess and an attached side portion shaped to match said recess, and the respective membranes are secured by their side edges between the wall portion so formed and the attached side wall portion.

6. An ultrasonic sensor of claim 5 wherein the arching of each membrane follows a circular arc and the attached side wall portions are in the shape of a segment of a circle.

7. An ultrasonic sensor of claim 1 wherein grooves are provided in each housing portion around the membrane to accommodate the sound-transmissive fluid contained by the membrane that is displaced upon insertion of a tube within the sensor.

8. An ultrasonic sensor of claim 7 wherein grooves that are rectangular in cross section are provided in the side walls of each housing portion.

9. An ultrasonic sensor of claim 7 wherein each of the membranes is arched along said side walls and grooves that are triangular in cross section are provided in the base of each housing portion.

10. An ultrasonic sensor of claim 1 wherein a pair of guide strips are provided in each housing portion above the membrane, which guide strips extend inwardly from the opposed side walls of the housing portion.

11. An ultrasonic sensor of claim 10 wherein said guide strips extend laterally far enough that they are adapted to reach said inserted tube.

12. An ultrasonic sensor of claim 11 wherein said guide strips are convexly inflected in their lengthwise direction.

13. An ultrasonic sensor of claim 1 wherein each of said membranes is comprised of a synthetic material having rubber-like elasticity.

14. An ultrasonic sensor of claim 1 wherein the two housing portions are hinged together by an articulation.

15. An ultrasonic sensor of claim 14 wherein a clasp is provided on the sides of the housing portions opposed to said articulation.

* * * * *